US011389120B2

(12) United States Patent
Sauser et al.

(10) Patent No.: US 11,389,120 B2
(45) Date of Patent: Jul. 19, 2022

(54) MATTRESS HAVING SELECTABLE PATIENT WEIGHT VALVE, INDUCTIVE POWER, AND A DIGITAL X-RAY CASSETTE (71) Applicant: Hill-Rom Services, Inc., Batesville, IN (US)

(72) Inventors: Frank E. Sauser, Cincinnati, OH (US); Charles A. Lachenbruch, Batesville, IN (US); Kathryn R. Smith, Batesville, IN (US); Jnanesha Ramegowda, Batesville, IN (US); Jason B. Grace, Cincinnati, OH (US); Douglas E. Borgman, Brookville, IN (US); Nolan D. Wanner, Milan, IN (US); Steven D. Baker, Beaverton, OR (US); Douglas A. Seim, Okeana, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 154 days.

(21) Appl. No.: 16/877,561

(22) Filed: May 19, 2020

(65) Prior Publication Data
US 2020/0375551 A1 Dec. 3, 2020

Related U.S. Application Data (60) Provisional application No. 62/854,497, filed on May 30, 2019.

(51) Int. Cl.
*A47C 27/10* (2006.01)
*A61B 6/04* (2006.01)
(Continued)

(52) U.S. Cl.
CPC .......... *A61B 6/0407* (2013.01); *A47C 27/007* (2013.01); *A47C 27/15* (2013.01);
(Continued)

(58) Field of Classification Search
CPC .. A61B 6/0407; A61G 7/0527; A47C 27/083; A47C 27/084; A47C 27/088; A47C 27/10; A47C 27/07
See application file for complete search history.

(56) References Cited

U.S. PATENT DOCUMENTS

| 4,539,560 A | 9/1985 | Fleck et al. |
| 4,934,468 A | 6/1990 | Koerber, Sr. et al. |
(Continued)

FOREIGN PATENT DOCUMENTS

| CA | 2159698 A1 | 5/1996 |
| EP | 1279393 A2 | 1/2003 |
(Continued)

OTHER PUBLICATIONS

U.S. Department of Health and Human Services, and U.S. Food and Drug Administration, Medical Bed Mattresses: FDA Safety Communication, "Damaged or Worn Covers Pose Risk of Contamination and Infection," Apr. 19, 2013, 1 page.

(Continued)

Primary Examiner — Fredrick C Conley
(74) Attorney, Agent, or Firm — Barnes & Thornburg LLP (57) ABSTRACT A patient support apparatus may include a foam frame defining a space. A bladder assembly may be positioned in the space. The bladder assembly may include a plurality of foam filled bladders. Each of the foam filled bladders may be interconnected by a manifold. A plurality of mutually exclusively selectable pressure relief valves may be provided to release air from the bladder assembly.

19 Claims, 10 Drawing Sheets (51) Int. Cl.
  *A61G 7/05* (2006.01)
  *A47C 27/00* (2006.01)
  *A47C 27/15* (2006.01)
(52) U.S. Cl.
  CPC .......... *A61G 7/0509* (2016.11); *A61G 7/0527* (2016.11); *A61G 2203/12* (2013.01); *A61G 2203/34* (2013.01); *A61G 2203/44* (2013.01)

(56) References Cited

U.S. PATENT DOCUMENTS

| | | | |
|---|---|---|---|
| 4,953,244 A | 9/1990 | Koerber, Sr. et al. | |
| 5,179,742 A | 1/1993 | Oberle | |
| 5,251,347 A | 10/1993 | Hopper et al. | |
| 5,325,551 A | 7/1994 | Tappel et al. | |
| 5,369,826 A | 12/1994 | Ikeda | |
| 5,377,369 A | 1/1995 | Shirai | |
| 5,377,373 A | 1/1995 | Shirai | |
| 5,388,290 A | 2/1995 | Shirai | |
| 5,483,709 A | 1/1996 | Foster et al. | |
| 5,542,136 A | 8/1996 | Tappel | |
| 5,630,238 A | 5/1997 | Weismiller et al. | |
| 5,634,224 A * | 6/1997 | Gates | A47C 27/081 5/654 |
| 5,666,681 A | 9/1997 | Meyer et al. | |
| 5,692,256 A | 12/1997 | Kramer et al. | |
| 5,715,548 A | 2/1998 | Weismiller et al. | |
| 5,794,288 A | 8/1998 | Soltani et al. | |
| 5,802,640 A | 9/1998 | Ferrand et al. | |
| 5,913,774 A | 6/1999 | Feddema | |
| 6,047,423 A | 4/2000 | Larson | |
| 6,073,289 A | 6/2000 | Bolden et al. | |
| 6,133,837 A | 10/2000 | Riley | |
| 6,182,316 B1 | 2/2001 | Thomas et al. | |
| 6,202,672 B1 | 3/2001 | Ellis et al. | |
| 6,208,250 B1 | 3/2001 | Dixon et al. | |
| 6,269,505 B1 * | 8/2001 | Wilkinson | A47C 27/084 5/654 |
| 6,499,167 B1 | 12/2002 | Ellis et al. | |
| 6,721,980 B1 * | 4/2004 | Price | A61B 5/0205 5/710 |
| 6,813,790 B2 | 11/2004 | Flick et al. | |
| 6,822,571 B2 | 11/2004 | Conway | |
| 6,826,795 B2 | 12/2004 | Wilkinson | |
| 7,191,482 B2 | 3/2007 | Romano et al. | |
| 2002/0129448 A1 * | 9/2002 | Pirzada | A47C 27/18 5/713 |
| 2005/0125905 A1 | 6/2005 | Wilkinson | |
| 2014/0223665 A1 * | 8/2014 | Chapin | A61G 7/05776 5/710 |
| 2016/0324707 A1 * | 11/2016 | Lachenbruch | A47C 27/10 |

FOREIGN PATENT DOCUMENTS

| | | |
|---|---|---|
| EP | 1820424 A2 | 8/2007 |
| JP | 6239863 B2 | 11/2017 |
| WO | 9949761 A1 | 10/1999 |

OTHER PUBLICATIONS

U.S. Department of Health and Human Services, and U.S. Food and Drug Administration, "Reprocessing Medical Devices in Health Care Settings: Validation Methods and Labeling: Guidance for Industry and Food and Drug Administration Staff," Mar. 17, 2015, 44 pages.

VanGilder, Catherine et al., "The International Pressure Ulcer Prevalence™ Survey: 2006-2015: A 10-Year Pressure Injury Prevalence and Demographic Trend Analysis by Care Setting," Journal of Wound, Ostomy and Continence Nursing Society (JWOCN), vol. 44(1):20-28, Jan./Feb. 2017, 9 pages.

VanGilder, Catherine et al., "Body Mass Index, Weight, and Pressure Ulcer Prevalence: An Analysis of the 2006-2007 International Pressure Ulcer Prevalence™ Surveys," Journal of Nursing Care Quality, vol. 24(2):127-135, Apr.-Jun. 2009, 9 pages.

* cited by examiner

MATTRESS HAVING SELECTABLE PATIENT WEIGHT VALVE, INDUCTIVE POWER, AND A DIGITAL X-RAY CASSETTE

CROSS-REFERENCE TO RELATED APPLICATIONS

This application claims priority under 35 U.S.C. § 119(e) to U.S. Provisional Patent Application Ser. No. 62/854,497, filed May 30, 2019, which is expressly incorporated by reference herein.

BACKGROUND

The disclosed embodiments are related to a patient support apparatus, and more particularly, to a patient support apparatus having a selectable patient weight valve, inductive power, and a digital x-ray cassette.

In some prior art surfaces, the support bladders have internal foam and a check valve that opens to release air once an internal pressure in the bladders reaches a predefined level. As a load is applied, the support bladders behave like air bladders with a given mid-range internal air pressure. At higher loads, the internal pressure forces the check valve open and the bladders drop into a second support behavior that is not augmented by air pressure.

Additionally, to better control a patient environment such as the mattress microclimate sensing of the mattress parameters is used. Examples of such sensing include humidity detection, airflow measurement, patient immersion sensing, temperature sensing and pressure mapping. For many of these, the sensors are positioned inside the mattress. The use of cables or wires to power the sensors presents a challenge of fatigue and/or damage.

Currently, a portable x-ray machine can be taken to the patient in a hospital bed or the emergency room. The x-ray tube is connected to a flexible arm that is extended over the patient while an x-ray film holder or image recording plate is placed beneath the patient. A challenge of doing in bed x-ray is that it is difficult to get the x-ray cassette beneath the patient. To do it safely it usually requires two hospital employees to lift the patient while the cassette is slid underneath. This can lead to caregiver/technician back injuries over time and inefficiency.

Another way in bed x-ray can be performed is using an x-ray sleeve in the surface. This makes it slightly easier to insert the cassette because the sleeve typically has low coefficient of friction (CoF) material and several layers of material between the patient and the cassette as a buffer. A challenge with this method is with new cleaning and disinfection (C&D) guidance from FDA. First, the sleeve needs to be wipeable for cleaning. Second, if the sleeve is not completely dried after cleaning, mold or bacteria growth may occur.

SUMMARY

The present disclosure includes one or more of the features recited in the appended claims and/or the following features which, alone or in any combination, may comprise patentable subject matter.

According to one aspect of the disclosed embodiments, a patient support apparatus may include a foam frame defining a space. A bladder assembly may be positioned in the space. The bladder assembly may include a plurality of foam filled bladders. Each of the foam filled bladders may be interconnected by a manifold. A plurality of mutually exclusively selectable pressure relief valves may be provided. A selected pressure release valve of the plurality of selectable pressure release valves may be configured to release air from the bladder assembly if a pressure in the bladder assembly exceeds a predetermined limit of the selected pressure relief valve. Each selectable pressure release valve may release air at a different predetermined limit.

In some embodiments, a control knob maybe used to select the selected pressure release valve. The control knob may be manually operated.

Optionally a weigh scale may be provided. The selected pressure relief valve may be selected based on a weight of a patient measured by the weigh scale. The selected pressure relief valve may be automatically selected based on the weight of the patient measured by the weigh scale.

It may be desired that the plurality of selectable pressure relief valves may include a first pressure relief valve having a predetermined limit that may correspond to a first weight of a patient. A second pressure relief valve may have a predetermined limit that corresponds to a second weight of a patient. A third pressure relief valve may have a predetermined limit that corresponds to a third weight of a patient. The first weight of the patient may be within a range of 70 pounds to 250 pounds. The second weight of the patient may be within a range of 251 pounds to 400 pounds. The third weight of the patient may be within a range of 401 pounds to 500 pounds.

It may be contemplated that the bladder assembly may include a first plurality of foam filled bladders and a second plurality of foam filled bladders. The plurality of selectable pressure release valves may include a first plurality of selectable pressure relief valves in fluid communication with the first plurality of foam filled bladders and a second plurality of selectable pressure relief valves in fluid communication with the second plurality of foam filled bladders. A first selected pressure release valve of the first plurality of selectable pressure release valves may configured to release air from the first plurality of foam filled bladders if the pressure in the first plurality of foam filled bladders exceeds a predetermined limit of the first selected pressure relief valve. A second selected pressure release valve of the second plurality of selectable pressure release valves may configured to release air from the second plurality of foam filled bladders if the pressure in the second plurality of foam filled bladders exceeds a predetermined limit of the second selected pressure relief valve. The predetermined limit of the first selected pressure relief valve may be different than the predetermined limit of the second selected pressure relief valve. The predetermined limit of the first selected pressure relief valve may be the same as the predetermined limit of the second selected pressure relief valve.

In some embodiments, a cover may encase the foam frame and the bladder assembly. An electronic component may be positioned within the cover. An inductive power receiver may be positioned within the cover. An inductive power transmitter may be positioned outside of the cover. The inductive power transmitter may transmit a power signal to the power transceiver to supply power to the electronic component. The electronic component may include a digital x-ray cassette. The electronic component may wirelessly transmit signals to devices positioned outside of the cover.

Optionally, the foam frame and the bladder assembly may be positioned on a frame. A side rail may be coupled to the frame. An inductive power transmitter may be positioned on the frame. An inductive power receiver may be positioned on the side rail. The inductive power transmitter may transmit a power signal to the inductive power receiver to power an electronic component on the side rail. The side rail may be moveable between a lowered position and a raised position. The inductive power transmitter may transmit a power signal to the inductive power receiver when the side rail is in the lowered position or the raised position.

According to another aspect of the disclosed embodiments, a patient support apparatus may include a foam frame defining a space. A bladder assembly may be positioned in the space. The bladder assembly may include a plurality of foam filled bladders. Each of the foam filled bladders may be interconnected by a manifold. An electronic pressure relief valve may have a pressure sensor. The electronic pressure relief valve may be configured to release air from the bladder assembly if the pressure sensor detects a pressure in the bladder assembly that exceeds a predetermined pressure.

In some embodiments, the electronic pressure relief valve may release air from the bladder assembly until a detected pressure in the bladder assembly equals the predetermined pressure. The predetermined pressure may be selectable based on a weight of a patient. The predetermined pressure may be manually selected.

Optionally, a weigh scale may be provided. The predetermined pressure may be selected based on a weight of a patient measured by the weigh scale. The predetermined pressure may be automatically selected based on the weight of the patient measured by the weigh scale.

It may be desired that a first predetermined pressure may correspond to a first weight of a patient. A second predetermined pressure may correspond to a second weight of a patient. A third predetermined pressure may correspond to a third weight of a patient. The first weight of the patient may be within a range of 70 pounds to 250 pounds. The second weight of the patient may be within a range of 251 pounds to 400 pounds. The third weight of the patient may be within a range of 401 pounds to 500 pounds.

It may be contemplated that the bladder assembly may include a first plurality of foam filled bladders and a second plurality of foam filled bladders. The electronic pressure relief valve may include a first electronic pressure relief valve in fluid communication with the first plurality of foam filled bladders and a second electronic pressure relief valve in fluid communication with the second plurality of foam filled bladders. The first electronic pressure relief valve may be configured to release air from the first plurality of foam filled bladders if the pressure in the first plurality of foam filled bladders exceeds a predetermined pressure of the first electronic pressure relief valve. The second electronic pressure relief valve may be configured to release air from the second plurality of foam filled bladders if the pressure in the second plurality of foam filled bladders exceeds a predetermined pressure of the second electronic pressure relief valve. The predetermined pressure of the first electronic pressure relief valve may be different than the predetermined pressure of the second electronic pressure relief valve. The predetermined pressure of the first electronic pressure relief valve may be the same as the predetermined pressure of the second electronic pressure relief valve.

In some embodiments, a cover may encase the foam frame and the bladder assembly. An electronic component may be positioned within the cover. An inductive power receiver may be positioned within the cover. An inductive power transmitter may be positioned outside of the cover. The inductive power transmitter may transmit a power signal to the power transceiver to supply power to the electronic component. The electronic component may include a digital x-ray cassette. The electronic component may wirelessly transmit signals to devices positioned outside of the cover.

Optionally, the foam frame and the bladder assembly may be positioned on a frame. A side rail may be coupled to the frame. An inductive power transmitter may be positioned on the frame. An inductive power receiver may be positioned on the side rail. The inductive power transmitter may transmit a power signal to the inductive power receiver to power an electronic component on the side rail.

According to yet another aspect of the disclosed embodiments, a patient support apparatus may include a frame. A mattress may be positioned on the frame. The mattress may have an electronic component positioned within an interior of the mattress. An inductive power transmitter may be coupled to the frame. An inductive power receiver may be positioned within the interior of the mattress and electrically coupled to the electronic component. The inductive power transmitter may transmit a power signal to the inductive power receiver to power the electronic component.

Optionally, the electronic component may include a sensor. The electronic components may include a digital x-ray cassette. The digital x-ray cassette may wirelessly transmit signals to a device outside of the mattress.

It may be desired that a side rail extends from the frame. A side rail inductive power receiver may be coupled to the side rail. The inductive power transmitter may transmit a power signal to the side rail inductive power receiver to power a side rail electronic component. The side rail electronic component may include a graphical user interface.

In some embodiments, the mattress further may include a foam frame defining a space. A bladder may be positioned in the space. A plurality of mutually exclusively selectable pressure relief valves. A selected pressure release valve of the plurality of selectable pressure release valves may be configured to release air from the bladder if a pressure in the bladder exceeds a predetermined limit of the selected pressure relief valve. Each selectable pressure release valve may release air at a different predetermined limit. The plurality of selectable pressure relief valves may include a first pressure relief valve having a predetermined limit that corresponds to a first weight of a patient. A second pressure relief valve may have a predetermined limit that corresponds to a second weight of a patient. A third pressure relief valve may have a predetermined limit that corresponds to a third weight of a patient. The first weight of the patient may be within a range of 70 pounds to 250 pounds. The second weight of the patient may be within a range of 251 pounds to 400 pounds. The third weight of the patient may be within a range of 401 pounds to 500 pounds.

It may be contemplated that the mattress includes a foam frame defining a space. A bladder may be positioned in the space. An electronic pressure relief valve may have a pressure sensor. The electronic pressure relief valve may be configured to release air from the bladder if the pressure sensor detects a pressure in the bladder that exceeds a predetermined pressure. A first predetermined pressure may correspond to a first weight of a patient. A second predetermined pressure may correspond to a second weight of a patient. A third predetermined pressure may correspond to a third weight of a patient. The first weight of the patient may be within a range of 70 pounds to 250 pounds. The second weight of the patient may be within a range of 251 pounds to 400 pounds. The third weight of the patient may be within a range of 401 pounds to 500 pounds.

In some embodiments, the mattress may include a foam frame defining a space. A bladder may be positioned in the space. A pressure relief valve may be configured to release air from the bladder if a pressure in the bladder exceeds a predetermined limit. The predetermined limit may be selected based on a weight of a patient. The predetermined limit may be manually selected. A weigh scale may be positioned between the frame and the mattress. The predetermined limit may be selected based on a weight of a patient as measured by the weigh scale.

According to a further aspect of the disclosed embodiments, a patient support apparatus may include a frame. A side rail may extend from the frame. An electronic component may be positioned on the side rail. An inductive power transmitter may be coupled to the frame. An inductive power receiver may be coupled to the side rail and electrically coupled to the electronic component. The inductive power transmitter may transmit a power signal to the inductive power receiver to power the electronic component.

It may be contemplated that the electronic component includes a graphical user interface. The electronic component may include a control system. The side rail may be moveable between a lowered position and a raised position. The power transmitter may transmit the power signal to the inductive power receiver when the side rail is in either the lowered position or the raised position. The side rail may be moveable to an intermediate position between the lowered position and the raised position. The inductive power transmitter may transmit the power signal to the inductive power receiver when the side rail is in the intermediate position.

It may be desired that a mattress may be positioned on the frame. The mattress may include a foam frame defining a space. A bladder may be positioned in the space. A plurality of mutually exclusively selectable pressure relief valves may be provided. A selected pressure release valve of the plurality of selectable pressure release valves may be configured to release air from the bladder if a pressure in the bladder exceeds a predetermined limit of the selected pressure relief valve. Each selectable pressure release valve may release air at a different predetermined limit. The plurality of mutually exclusively selectable pressure relief valves may include a first pressure relief valve having a predetermined limit that corresponds to a first weight of a patient. A second pressure relief valve may have a predetermined limit that corresponds to a second weight of a patient. A third pressure relief valve may have a predetermined limit that corresponds to a third weight of a patient. The first weight of the patient may be within a range of 70 pounds to 250 pounds. The second weight of the patient may be within a range of 251 pounds to 400 pounds. The third weight of the patient may be within a range of 401 pounds to 500 pounds.

In some embodiments, a mattress may be positioned on the frame. The mattress may include a foam frame defining a space. A bladder may be positioned in the space. An electronic pressure relief valve may have a pressure sensor. The electronic pressure relief valve may be configured to release air from the bladder if the pressure sensor detects a pressure in the bladder that exceeds a predetermined pressure. A first predetermined pressure may correspond to a first weight of a patient. A second predetermined pressure may correspond to a second weight of a patient. A third predetermined pressure may correspond to a third weight of a patient. The first weight of the patient may be within a range of 70 pounds to 250 pounds. The second weight of the patient may be within a range of 251 pounds to 400 pounds. The third weight of the patient may be within a range of 401 pounds to 500 pounds.

Optionally, a mattress may be positioned on the frame. The mattress may include a foam frame defining a space. A bladder may be positioned in the space. A pressure relief valve may be configured to release air from the bladder if a pressure in the bladder exceeds a predetermined limit. The predetermined limit may selected based on a weight of a patient. The predetermined limit may be manually selected. A weigh scale may be positioned on the frame. The predetermined limit may be selected based on a weight of a patient as measured by the weigh scale. The predetermined limit may be automatically selected.

According to yet a further aspect of the disclosed embodiments, a patient support apparatus may include a patient support. A cover may enclose the patient support. An x-ray cassette may be positioned within the cover. A wireless transceiver may be coupled to the x-ray cassette. The wireless transceiver may wirelessly communicate signals between the x-ray cassette and a device positioned outside of the cover. The x-ray cassette may include a digital x-ray cassette.

In some embodiments, an inductive power receiver may be positioned within the cover and may be configured to receive power signals from an inductive power transmitter positioned outside of the cover. The x-ray cassette may be powered by the inductive power receiver. An electronic component may be positioned within the cover. The electronic component may be powered by the inductive power receiver. The electronic component may include a sensor. The device may include an x-ray control module.

Optionally, a foam frame may define a space. A bladder may be positioned in the space. A pressure relief valve may be configured to release air from the bladder if a pressure in the bladder exceeds a predetermined limit. The predetermined limit may be selected based on a weight of a patient. The predetermined limit may be manually selected. A weigh scale may be positioned on the frame. The predetermined limit may be selected based on a weight of a patient as measured by the weigh scale. The predetermined limit may be automatically selected. A first predetermined limit may correspond to a first weight of a patient. A second predetermined limit may correspond to a second weight of a patient. A third predetermined limit may correspond to a third weight of a patient. The first weight of the patient may be within a range of 70 pounds to 250 pounds. The second weight of the patient may be within a range of 251 pounds to 400 pounds. The third weight of the patient may be within a range of 401 pounds to 500 pounds.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
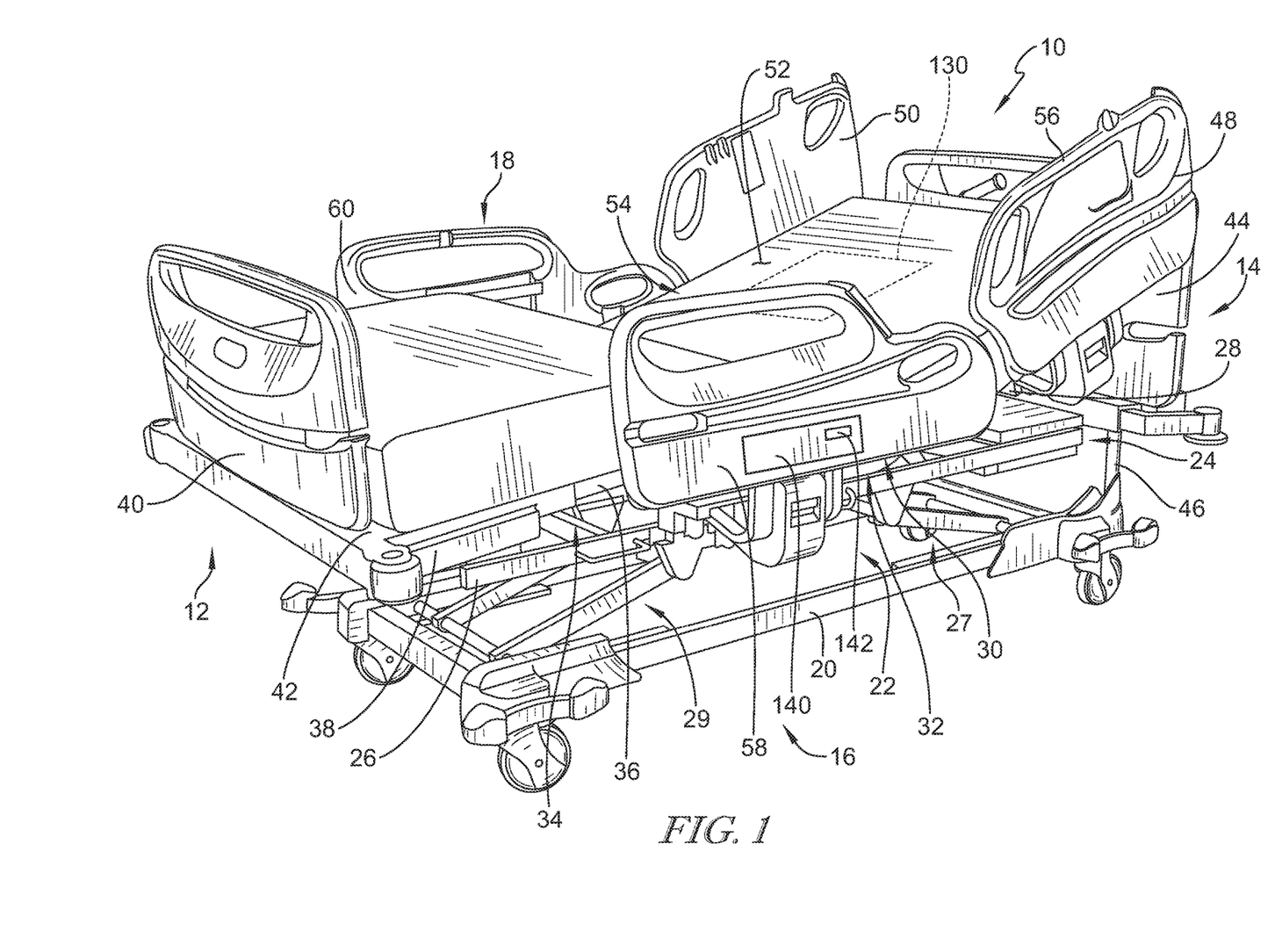
FIG. 1 is a side perspective view of a patient support apparatus in accordance with an embodiment and having a mattress positioned on top of a frame.

Referring to FIG. 1, a patient support apparatus 10 is illustratively embodied as a hospital bed 10. The view shown in FIG. 1 is generally taken from a position that is oriented at the left side, foot end of the hospital bed 10. For purposes of orientation, the discussion of the hospital bed 10 will be based on the orientation of a patient supported on the hospital bed 10 in a supine position. Thus, the foot end 12 of the hospital bed 10 refers to the end nearest the patient's feet when the patient is supported on the hospital bed 10 in the supine position. The hospital bed 10 has a head end 14 opposite the foot end 12. A left side 16 refers to the patient's left when the patient is lying in the hospital bed 10 in a supine position. The right side 18 refers to the patient's right. When reference is made to the longitudinal length of the hospital bed 10, it refers a direction that is represented by the lines that generally extend between the head end 14 and foot end 12 of the hospital bed 10. Similarly, lateral width of the hospital bed 10 refers to a direction that is represented by the lines that generally extend between the left side 16 and right side 18.

The hospital bed 10 includes a base frame 20, which supports a lift system 22. The lift system 22 engages the base and an upper frame 24 such that the lift system 22 moves the upper frame 24 vertically relative to the base frame 20. The lift system 22 includes a head end linkage 27 and a foot end linkage 29. Each of the linkages 27 and 29 are independently operable and may be operated to cause the hospital bed 10 to move into a tilt position which is when the head end 14 of the upper frame 24 is positioned lower than the foot end 12 of the upper frame 24. The hospital bed 10 may also be moved to a reverse tilt position with the foot end 12 of the upper frame 24 is positioned lower than the head end 14 of the upper frame 24.

The upper frame 24 supports a load frame 26. The load frame 26 supports a head deck 28 which is movable relative to the load frame 26. The load frame 26 also supports an articulated seat deck 30, also movable relative to the load frame 26 and a fixed seat deck 32. Also supported from the load frame 26 is a foot deck 34 that is articulated and moveable relative to the load frame 26. The foot deck 34 in the illustrative embodiment of FIG. 1 provides for powered pivoting of the foot deck 34 and manual extension and retraction of the foot deck 34 to vary the length of the foot deck 34. In other embodiments, powered pivoting of the foot deck 34 may be omitted and the related movement may be caused manually, or follow movement of the articulated seat deck 30. In addition, in some embodiments, extension and retraction of the foot deck 34 may be powered by an actuator.

The foot deck 34 includes a first portion 36 and a second portion 38, which moves relative to the first portion 36 to vary the size of the foot deck 34. The second portion 38 moves generally longitudinally relative to the first portion 36 to vary the longitudinal length of the foot deck 34 and, thereby, the longitudinal length of the hospital bed 10.

A foot panel 40 is supported from the second portion 38 and extends vertically from an upper surface 42 of the second portion 38 to form a barrier at the foot end 12 of the hospital bed 10. A head panel 44 is positioned on an upright structure 46 of the base frame 20 and extends vertically to form a barrier at the head end 14 of the hospital bed 10. A left head side rail 48 is supported from the head deck 28 and is moveable between a raised position shown in FIG. 1 and a lowered position as is known in the art. A right head side rail 50 is also moveable between the raised position of FIG. 1 and lowered position. As shown in FIG. 1, in the raised position, the side rails 48 and 50 extend above an upper surface 52 of a mattress 54 of the hospital bed 10 when the side rails 48 and 50 are in a raised position. In a lowered position an upper edge 56 of the left head side rail 48 is below the upper surface 52. It should be appreciated that in some embodiments, the left head side rail 48 and the right head side rail 50 are movable to a position between the raised position and the lowered position.

The hospital bed 10 also includes a left foot side rail 58 and a right foot side rail 60, each of which is supported directly from the load frame 26. Each of the side rails 48, 50, 58, and 60 are operable to be lowered to a position below the upper surface 52. It should be appreciated that in some embodiments, the left foot side rail 58 and the right foot side rail 60 are movable to a position between the raised position and the lowered position. It should be noted that when the head deck 28 is moved, the head side rails 48 and 50 move with the head deck 28 so that they maintain their relative position to the patient. This is because both of the head side rails 48 and 50 are supported by the head deck 28.

In the illustrative embodiment, a weigh scale 130 is positioned between the mattress 54 and the upper frame 24. In some embodiments, the weigh scale 130 may be positioned within the mattress 54. The weigh scale 130 measures a weight of a patient on the mattress 54. The weigh scale 130 may also measure a distribution of the patient's weight. For example, the weigh scale 130 may determine that the patient is applying a 30 pound force on the head deck 28 and 80 pounds of force on the seat deck 30.

A control system 140 may be embedded in one of the side rails 48, 50, 58, and 60. A graphical user interface 142 is electronically coupled to the control system 140 so that a user, e.g. the caregiver or patient, can operate the bed 10. For example, the graphical user interface 142 may include buttons or icons configured to control movement of the various sections of the bed 10. The graphical user interface 142 transmits a signal to the control system 140 indicative of the desired movement and the control system 140 operates the various motors and actuators to move the sections of the bed 10. In some embodiments, the graphical user interface 142 may also display outputs from various sensors in the bed 10, e.g. a patient weight or vital signs.

Figure 2:
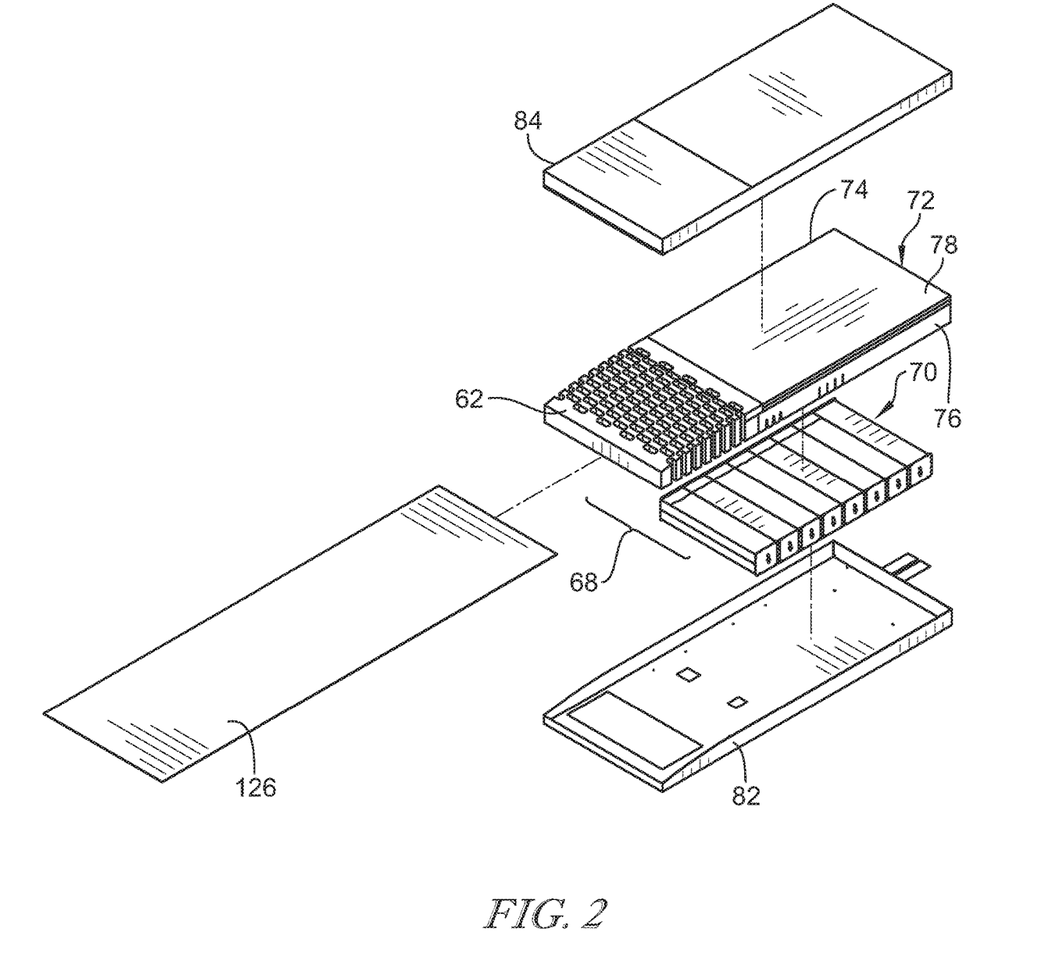
FIG. 2 is an exploded view of the mattress shown in FIG. 1 and having a foam structure surrounding a bladder assembly, wherein the foam structure and bladder assembly are configured to be encased by a fire sock and a cover.
Figure 3:
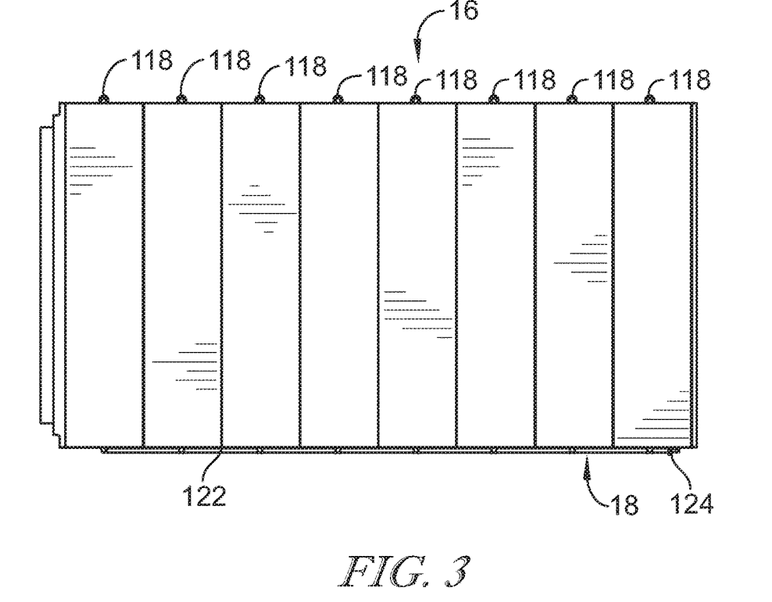
FIG. 3 is a top plan view of the bladder assembly shown in FIG. 2 and having a manifold coupled to a pressure relief valve assembly.
Figure 4:
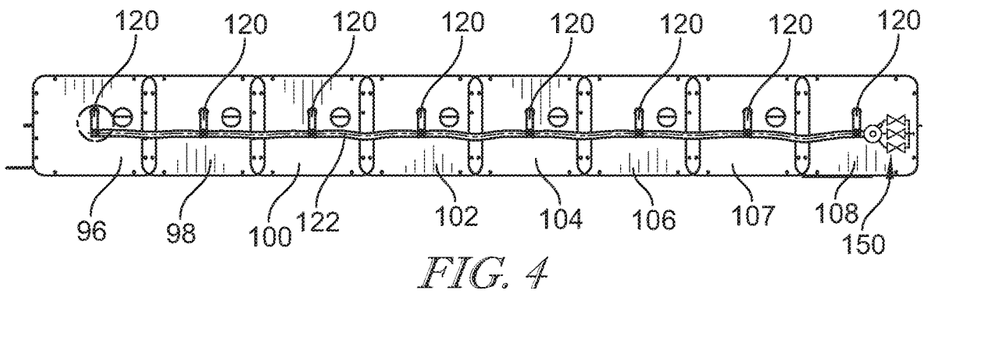
FIG. 4 is a side elevation view of the bladder assembly shown in FIG. 3 and showing the manifold coupled to the pressure relief valve assembly.

Referring to FIGS. 2-4, the mattress 54 includes a core 68 which comprises a bladder assembly 70 which engages a foam frame 72. The foam frame 72 includes a perforated foot support 62 which is coupled to a pair of longitudinal bolsters 74 and 76. The longitudinal bolsters 74, 76 are interconnected by a header 78 which extends laterally between the bolsters 74, 76 at the head end 14 of the mattress 54. The core 68 also includes an upper layer of foam and a lower layer of foam which are glued together to form an upper foam support. The longitudinal bolsters 74 and 76 are secured to the perforated foot support 62 such that the foot support 62, bolsters 74 and 76, header 78, and foam support cooperate to define a space into which the bladder assembly 70 is positioned to form the core 68. The mattress 54 includes a lower cover 82 and an upper cover 84 which are secured together with a zipper as is known in the art. The mattress 54 further includes a fire barrier assembly 126 which is wrapped over the top of core 68 to fully enclose the core 68 in the fire barrier assembly 126.

The bladder assembly 70 includes eight bladders 96, 98, 100, 102, 104, 106, 107, and 108. The bladders are arranged with bladder 108 positioned at the foot end 12 of the bladder assembly 70 and bladder 96 positioned at the head end 14. Each bladder 96, 98, 100, 102, 104, 106, 107, and 108 comprises an outer layer of urethane-coated nylon, which provides an air impermeable foam-filled bladder 110. Inside of each foam-filled bladder 110 is a two layered foam structure. The foam structure includes an upper layer and a lower layer. The foam layers and are glued together. The foam structure is deformable under load, but resiliently expands to fill the interior space of the foam-filled bladder 110.

At the left side 16 of each foam-filled bladder 110 is a pressure relief or check valve 118. Each of the check valves 118 are configured to open when the pressure applied to the valve exceeds the relief pressure of the valve 118. In the arrangement of the bladder assembly 70, the valves 118 are arranged such that when the pressure inside any one of the foam-filled bladders 110 is lower than the pressure of atmosphere, the corresponding valve 118 opens to permit air to flow from atmosphere into the respective foam-filled bladder 110.

On the right side 18 of the bladder assembly 70, each foam-filled bladder 110 includes a respective outlet 120. Each of the outlets 120 are connected to a manifold tube 122 so that the foam-filled bladders 110 are all in fluid communication with one another through the outlets 120 and manifold tube 122. The manifold tube 122 terminates with a relief valve assembly 150. The relief valve assembly 150 is configured such that, when the pressure in the manifold tube exceeds a relief pressure of the relief valve assembly 150, the relief valve assembly 150 opens to permit the venting of the pressure to atmosphere. It should be understood that the valves 118, being check valves, do not permit a flow of air from the foam-filled bladders 110 through the valves 118 to atmosphere. The only flow path for air from the foam-filled bladders 110 to atmosphere is through the manifold tube 122 and relief valve assembly 150. Similarly, the only path for that flow into any of the foam-filled bladders 110 is through a respective valve 118.

Thus, the mattress 54 is configured to maintain the pressure within each of the bladders 96, 98, 100, 102, 104, 106, 107, and 108 to a pressure below the relief pressure of the relief valve assembly 150 and above the activation pressure of inlet valves 118. The operation of the inlet valves 118 of any particular bladder 96, 98, 100, 102, 104, 106, 107, and 108, which is unloaded, provides for the rapid filling of the respective bladder 96, 98, 100, 102, 104, 106, 107, and 108 with air from atmosphere. This approach helps to regulate the pressure within the various bladders 96, 98, 100, 102, 104, 106, 107, and 108 relatively quickly to control the support pressure experienced by a patient.

In the event that the patient exceeds the weight corresponding to the relief pressures of the bladder assembly 70, venting of the pressure in the manifold tube 122 and relief valve assembly 150 permits the patient to be supported on the foam structures of each bladder 96, 98, 100, 102, 104, 106, 107, and 108. In this way, the mattress 54 provides the benefits of a pneumatic mattress with safety for larger patients from bottoming out against the surface of the decks of the hospital bed 10. It should be understood that the foam structures also serve the purpose of expanding the foam-filled bladders 110 to create the vacuum, which draws air through the valves 118 when a particular bladder 96, 98, 100, 102, 104, 106, 107, and 108 is unloaded.

Figure 5:
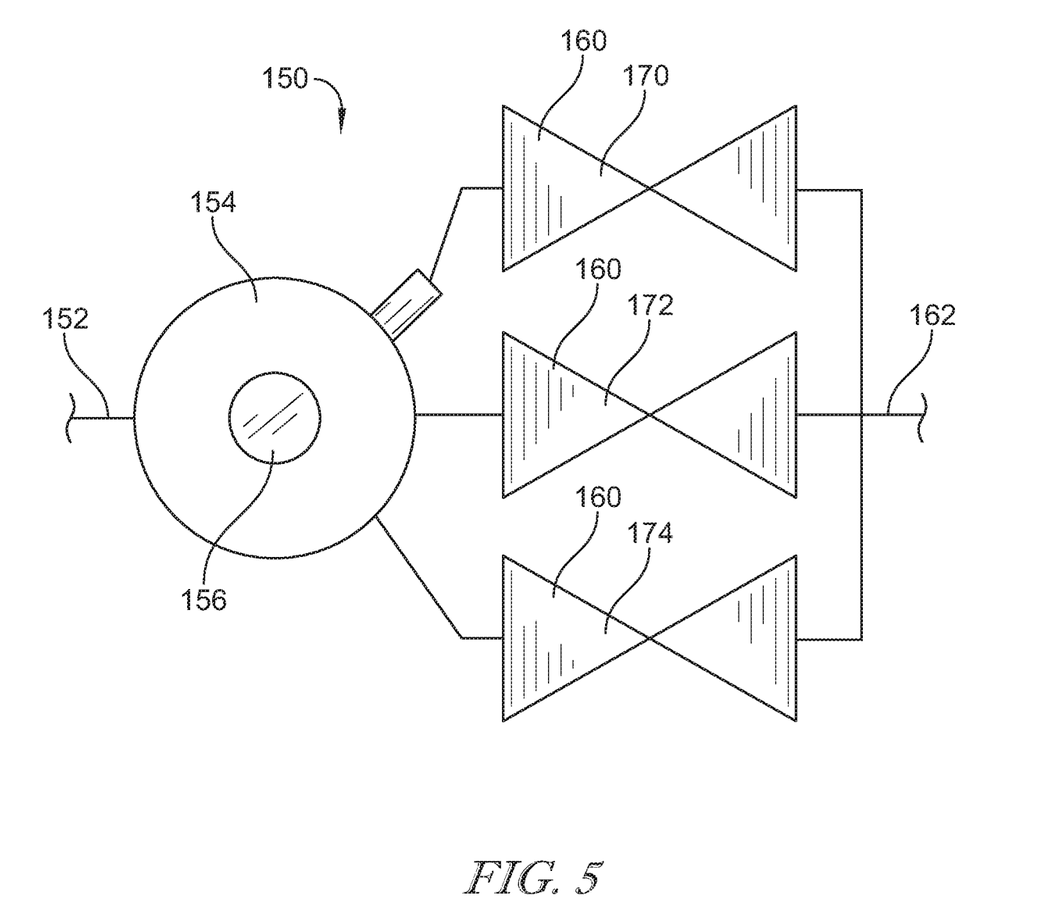
FIG. 5 is a schematic view of an embodiment of the pressure relief valve assembly having a control knob to select one of a plurality of mutually exclusive pressure relief valves.

Referring now to FIG. 5, the relief valve assembly 150 includes an inlet 152 fluidly coupled to a switch 154. The switch 154 is a manual switch that is operated by rotating a dial 156. Outlets 158 extend from the switch 154 to a plurality of mutually exclusive pressure relief valves 160. By rotating the dial 156, a user can select a pressure relief valve 160. The pressure relief valve 160 is selected based on a weight of the patient. For example, the patient may be weighed prior to being positioned on the bed 10. In another embodiment, the patient may be weighed by the weigh scale 130. The caregiver, then selects the appropriate pressure relief valve 160 based on the patient's weight. It may be contemplated that the dial is automatically triggered to select a pressure relief valve 160 based on a weight of the patient as measured by the weigh scale 130. Each pressure relief valve 160 is coupled to an outlet 162 of the relief valve assembly 150.

Each pressure relief valve 160 corresponds to a weight range of the patient. For example, a first pressure relief valve 170 may be selected for patients weighing within a range of 70 pounds to 250 pounds. A second pressure relief valve 172 may be selected for patients weighing within a range of 251 pounds to 400 pounds. A third pressure relief valve 174 may be selected for patients weighing within a range of 401 pounds to 500 pounds. In another embodiment, the first pressure relief valve 170 may be selected for patients weighing between 141 pounds and 180 pounds. The second pressure relief valve 172 may be selected for patients weighing between 181 pounds and 250 pounds. The third pressure relief valve 174 may be selected for patients weighing over 253 pounds. It will be appreciated that the pressure relief valves 170, 172, 174 may be set for any desirable range of patient weight.

Each pressure relief valve 160 is configured to maintain the pressure within each of the bladders 96, 98, 100, 102, 104, 106, 107, and 108 to a pressure below a relief pressure of the pressure relief valve 160. Each pressure relief valve 160 has a different relief pressure that corresponds to the weight range of the respective pressure relief valve 160. The first pressure relief valve 170 may have a relief pressure that is less than the relief pressure of the second pressure relief valve 172. The second pressure relief valve 172 may have a relief pressure that is less than the relief pressure of the third pressure relief valve 174.

Figure 6:
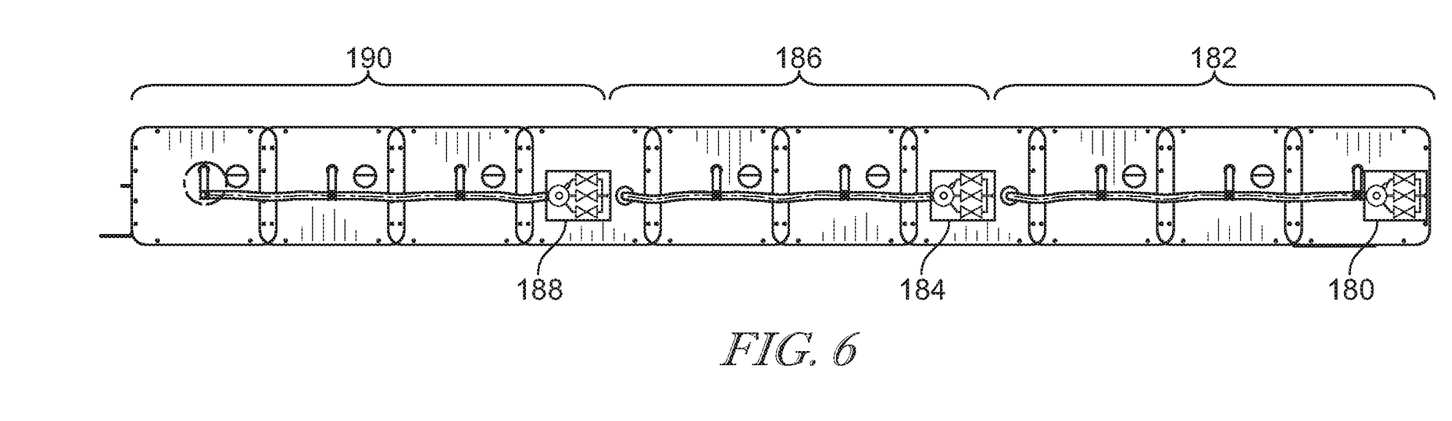
FIG. 6 is a side elevation view of the bladder assembly shown in FIG. 3 and showing the manifold coupled to the a plurality of pressure relief valve assemblies.

In some embodiments, the mattress 54 includes a plurality of relief valve assemblies 150. For example, as shown in FIG. 6, a head relief valve assembly 180 may control the pressure relief of bladders 182 in a head section of the mattress 54, a seat relief valve assembly 184 may control the pressure relief of bladders 186 in a seat section of the mattress 54, and a foot relief valve assembly 188 may control pressure relief in a foot section 190 of the mattress 54. In such an embodiment, each relief valve assembly 180, 184, 186 may be set to the same relief pressure. Alternatively, each relief valve assembly 180, 184, 186 may be set to a different relief pressure. In some embodiments, some relief valve assemblies 180, 184, 186 may be set to the same relief pressure, while other relief valve assemblies are set to a different relief pressure.

Figure 7:
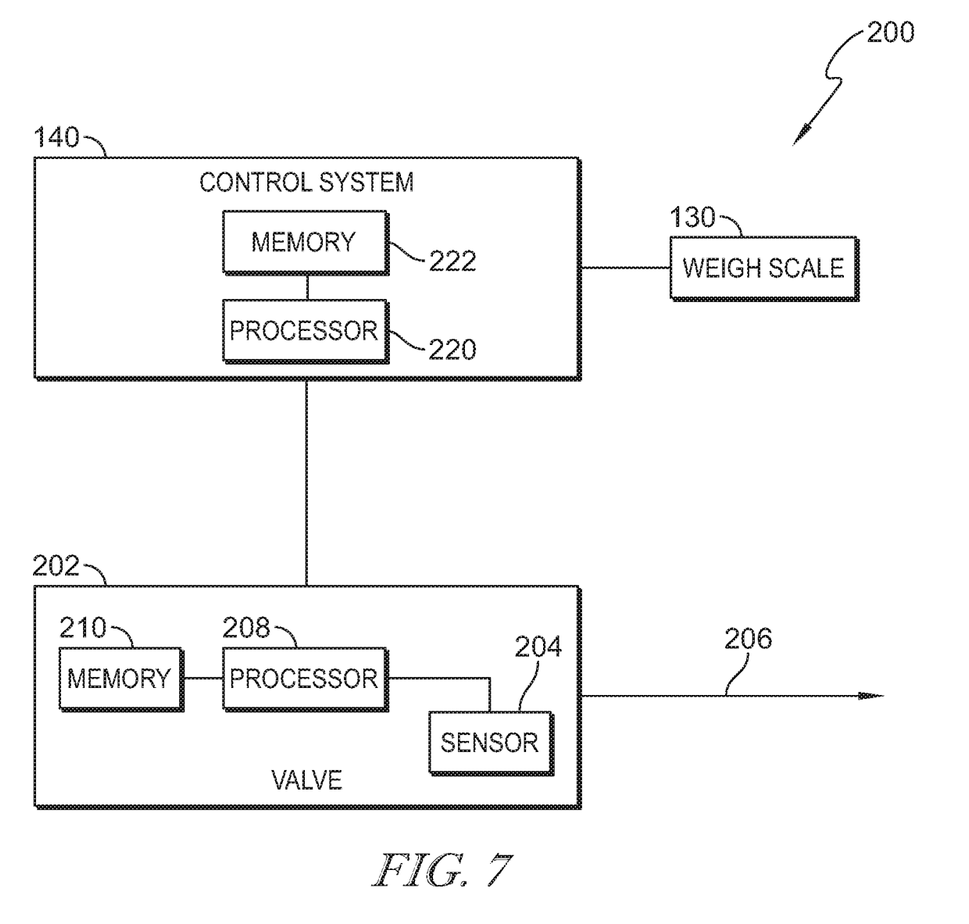
FIG. 7 is a schematic view of another embodiment of the pressure relief valve assembly having an electronic pressure relief valve and pressure sensor.

Referring to FIG. 7, a relief valve assembly 200 may be used in place of the relief valve assembly 150. The relief valve assembly 200 includes an electric valve 202 that is configured to discharge air from the bladders 96, 98, 100, 102, 104, 106, 107, and 108 through an outlet 206 to a pressure below a relief pressure. The assembly 200 includes a pressure sensor 204 that determines a pressure within the bladders 96, 98, 100, 102, 104, 106, 107, and 108. When the pressure sensor 204 detects a pressure that is greater than the relief pressure, the electric valve 202 is opened to discharge air from the bladders 96, 98, 100, 102, 104, 106, 107, and 108 until the pressure drops. In some embodiments, the plurality of relief valve assemblies 180, 184, 186 shown in FIG. 6 may utilize an electric valve 202 as described above.

Figure 8:
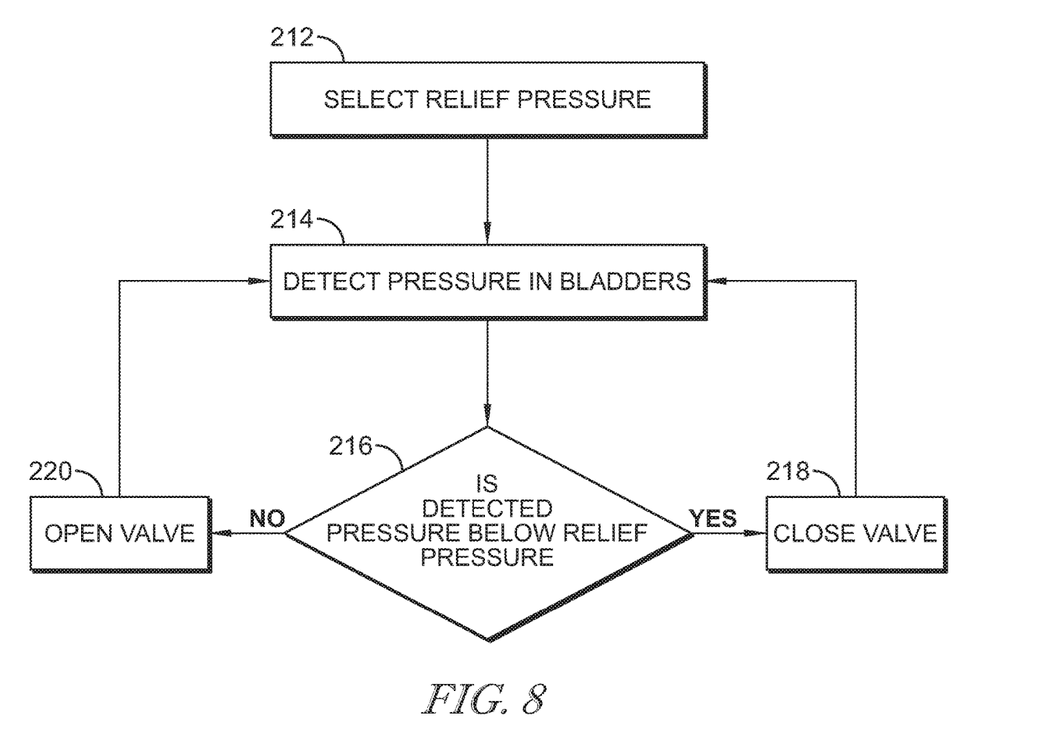
FIG. 8 is a flowchart illustrating operation of the pressure relief valve assembly shown in FIG. 7.

The relief valve assembly 200 includes a processor 208 and a memory 210. The memory 210 stores instructions that are carried out by the processor 208. FIG. 8 illustrates an algorithm operated by the processor 208. At step 212, a relief pressure for the bladders 96, 98, 100, 102, 104, 106, 107, and 108 is selected as set forth below. At step 214, the pressure sensor 204 detects a pressure in the bladders 96, 98, 100, 102, 104, 106, 107, and 108. The detected pressure is compared to the relief pressure, at step 216. If the detected pressure is below the relief pressure, the valve 202 remains closed, at step 218. If the detected pressure is above the relief pressure, the valve 202 is opened to release air from the bladders 96, 98, 100, 102, 104, 106, 107, and 108. The sensor 204, then continues to detect the pressure in the bladders 96, 98, 100, 102, 104, 106, 107, and 108, at step 214. Accordingly, if the valve 202 is opened, it only remains open until the detected pressure is below the relief pressure.

The relief pressure may be altered based on the weight of the patient, as set forth above. For example, a caregiver may enter the patient's weight into the control system 140 using the graphical user interface 142. Based on this weight, the control system 140 may alter the relief pressure of the assembly 200. That is, the pressure required to be detected by the pressure sensor 204 before opening the electric valve is altered based on the weight of the patient.

In some embodiments, the relief pressure is automatically altered based on a weight of the patient as measured by the weigh scale 130. In such an embodiment, the weigh scale 130 transmits a data signal to the control system 140. The data signal is indicative of a weight of the patient as measured by the weigh scale 130. The control system 140 includes a processor 220 and a memory 222. The memory 222 includes instructions that, when executed by the processor 220, cause the control system 140 to transmit a data signal to the relief valve assembly 200 to alter the relief pressure of the assembly 200 based on the weight of the patient as measured by the weigh scale 130.

The bladder behavior for any given surface must fall into two distinct ranges. A first range is when the check valve is closed and all pressures in the bladders are less than the relief pressure. In this range air pressure dominates the behavior of the surface. In a second range, the check valve is open and the pressures are greater than the relief pressure. In this range, the surface behavior is dominated by the foam(s) within the support bladders. The embodiments described herein introduce a third state where a selectable check valve with a small differential between the relief pressure and reseal pressure allows air to escape to a controlled pressure. Accordingly, the check valve reseal pressure creates the third state with partial air and partial foam support. Another embodiment includes multi-zoned selectable pressures that includes a check valve at one or more individual zones.

Using selectable check valves provides a non-powered solution to patient comfort adjustment. By selecting a check valve with a higher reseal pressure, a patient or caregiver could choose a firmer surface. By selecting a check valve with a lower reseal pressure, the patient or caregiver could choose a softer surface.

Figure 9:
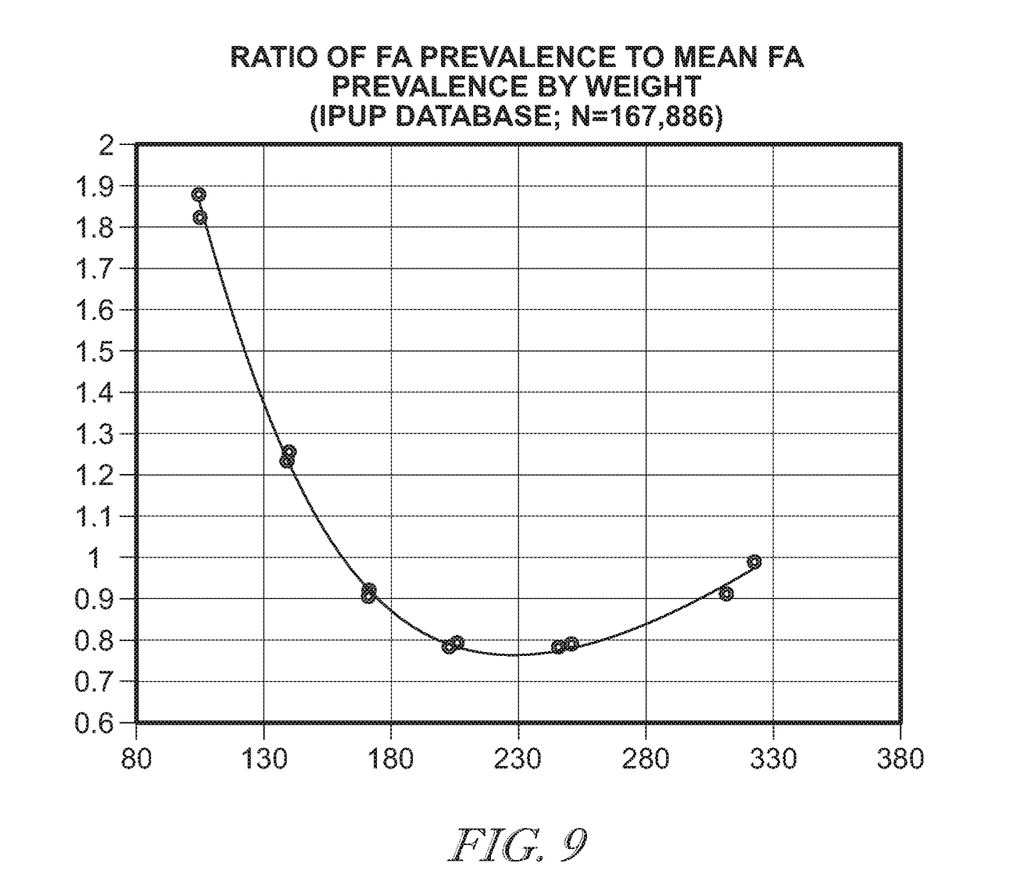
FIG. 9 is a graph illustrating the ratio of pressure ulcer prevalence to mean pressure ulcer prevalence as a function of patient weight.

The selectable ranges enable a caregiver or patient to hone in on an optimal set of support pressures for each patient weight. The tendency in unpowered products, due to general patient weight increases over the last several years, has been to broaden the target range for each product. Typically, this means broadening the target weight range from 100 to 300 up to 100 to 500 lbs. However, because risk of pressure injury in the patient is a U-shaped phenomenon with very high risk in the 100-140 lbs. range (as illustrated in FIG. 9), broadening the target weight range increases prevalence in low weight patients to accommodate patients between 300 and 500 lbs.

Figure 10:
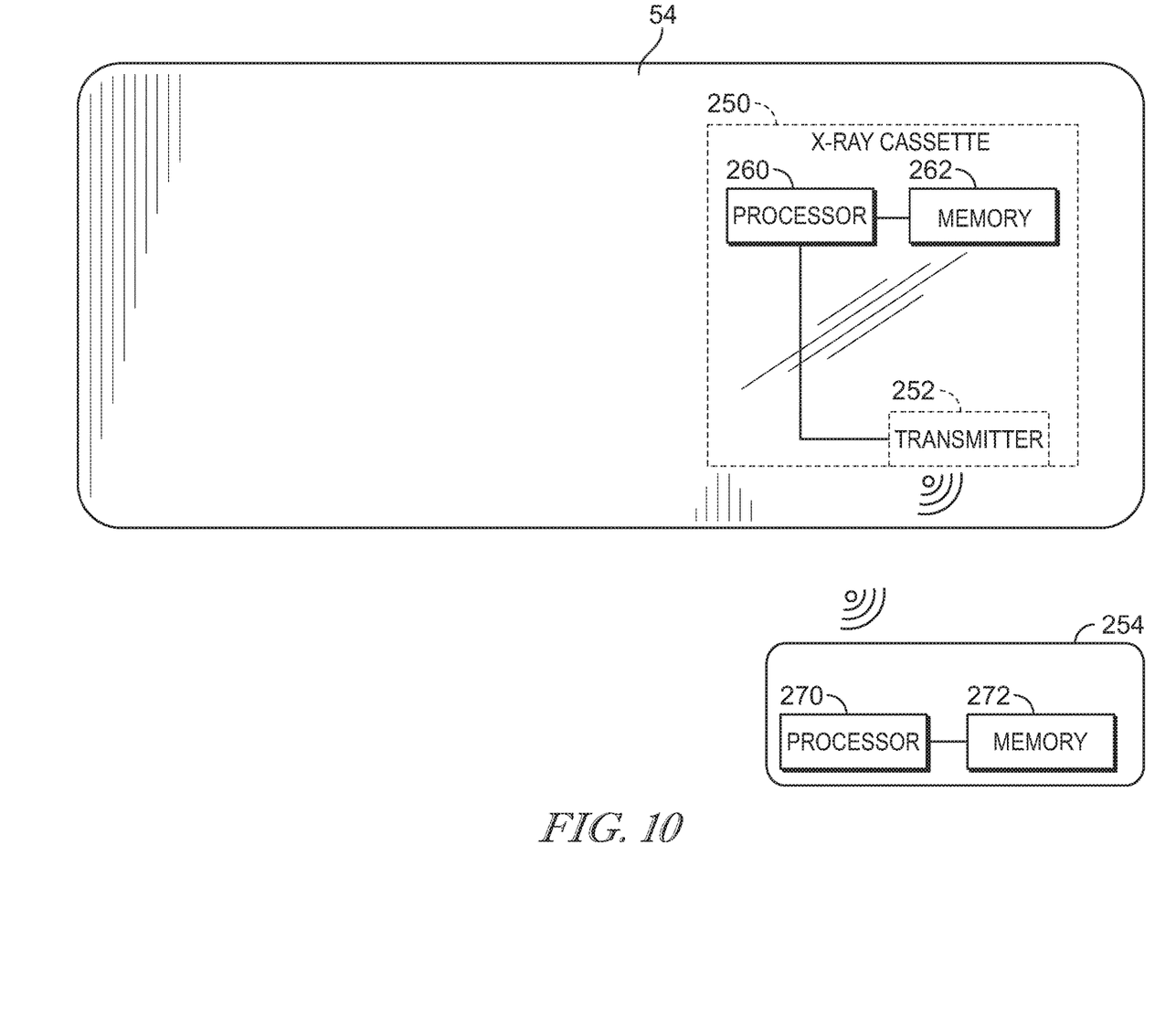
FIG. 10 is a top plan view of the mattress shown in FIG. 1 having a digital x-ray cassette positioned within a cover of the mattress.

Referring now to FIG. 10, the mattress 54 may include a digital x-ray cassette 250 positioned within the mattress 54. The digital x-ray cassette 250 is sealed within the mattress 54 and configured to take x-rays of the patient without having to move the patient. The cassette 250 includes a processor 260 and a memory 262. The cassette 250 includes a wireless transmitter 252 that is configured to transmit data signals from the cassette 250 to a device 254 positioned outside of the mattress 54. The device 254 includes a processor 270 and a memory 272. For example, the device 254 may be an x-ray control module that reads the x-rays taken by the cassette 250. Additionally, the data signals may be sent to remote computers, such as a nurse's station, a doctor's office, or an electronic medical record.

The digital x-ray cassette 250 is integrated into the patient support surface to wirelessly communicate with a portable x-ray machine or hospital electronic medical record. In an air surface the rigid digital cassette 250 could be fabricated into the bottom of the mattress 54 to remove any potential interference with a microclimate management system or interface pressure performance. During an X-ray the air bladders could be softened or reduced in air pressure to bring the patient in closer proximity for image quality. In some embodiments, the cassette 250 may be developed into a flexible format so that the x-ray cassette 250 could be closer to the patient within the mattress 54. Accordingly, an x-ray could be taken with no need to deflate the mattress or reposition the patient.

In an embodiment where the device 254 is an x-ray control module, the device 254 may be positioned over the cassette 250 so that the patient is positioned between the device 254 and the cassette 250. The cassette 250 is then powered, for example through inductive power as described in more detail below. It should be noted that the cassette 250 need only be powered when x-rays are being taken. To save energy, the cassette may be turned off when not in use. Once in position with the cassette powered, the device 254 sends x-rays to the cassette 250. The cassette 250 detects the x-rays and produces image data related to an image produced by the x-ray. The cassette 250 wirelessly transmits the image data to the device 254. An image is then produced at the device 254 or on another display coupled to the device 254 based on the image data.

With the cassette 250 there is no need to move the patient to insert the cassette so back injuries to caregiver may be avoided. The cassette 250 also reduces patient discomfort by removing the step of moving the patient. Additionally, cleaning and disinfection concerns with the cassette and x-ray sleeve are eliminated. And, the potential for indirect or direct patient contact to the cassette is eliminated to prevent any cross-contamination between patients.

Figure 11:
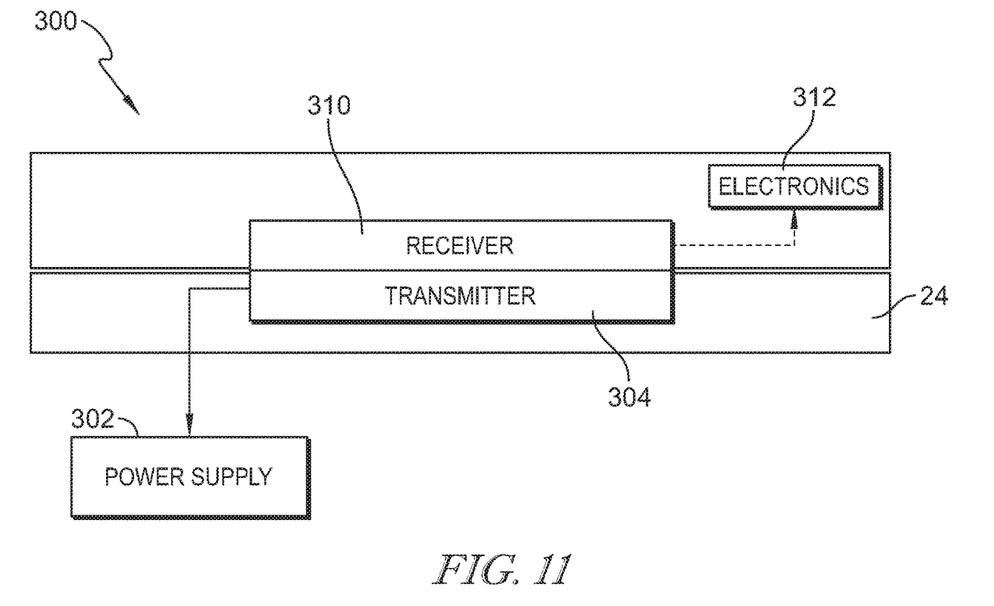
FIG. 11 is a side schematic view of the mattress shown in FIG. 1 positioned on the frame shown in FIG. 1 and an inductive power transmitter positioned on the frame and an inductive power receiver positioned within the mattress.

FIG. 11 illustrates an inductive power system 300 of the bed 10. The upper frame 24 of the bed includes a power supply 302. The power supply 302 may be electrically coupled to various electronics of the bed 10, e.g. the control system 140 and the graphical user interface 142. The power supply 302 is plugged into a power supply of the room, for example, a wall outlet. An inductive power transmitter 304 is electrically coupled to the power supply 302. The transmitter 304 is positioned beneath the mattress 54.

The mattress 54 includes an inductive power receiver 310 that is positioned within the mattress 54. The receiver 310 is coupled to various electronics 312 positioned within the mattress 54. The electronics 312 may include a plurality of sensors, for the mattress 54. The sensors may include humidity sensors, temperature sensors, pressures sensors, or the like. In some embodiments, the electronics 312 include the digital x-ray cassette 250.

The power transmitter 304 inductively passes power to the power receiver 310 to wirelessly power the electronics 312 of the mattress 54 without having to pass wires through the mattress cover. In some embodiments, data may be transmitted between the transmitter 304 and the receiver 310. It will be appreciated that both the transmitter 304 and the receiver 310 may be transceivers capable of both transmitting and receiving power and data. As such, data from the electronics 312 may be transmitted to the control system 140 of the bed 10 and displayed on the graphical user interface 142.

The transmitter 304 is a flat pad that rests on the top of the frame 24, directly below the mattress 54. The transmitter pad 304 is connected to the bed power 302 and communications bus. The other side 310 of the wireless power/data system 300 is inside of the bottom ticking and may be connected to any sensors inside the mattress 54 (humidity, air flow, temperature, radar, accelerometer, etc). Electronics inside the ticking might also include an energy storage device 320 such as a battery or super-cap so that peak power needs are met with a relatively small wireless power/data system.

Figure 12:
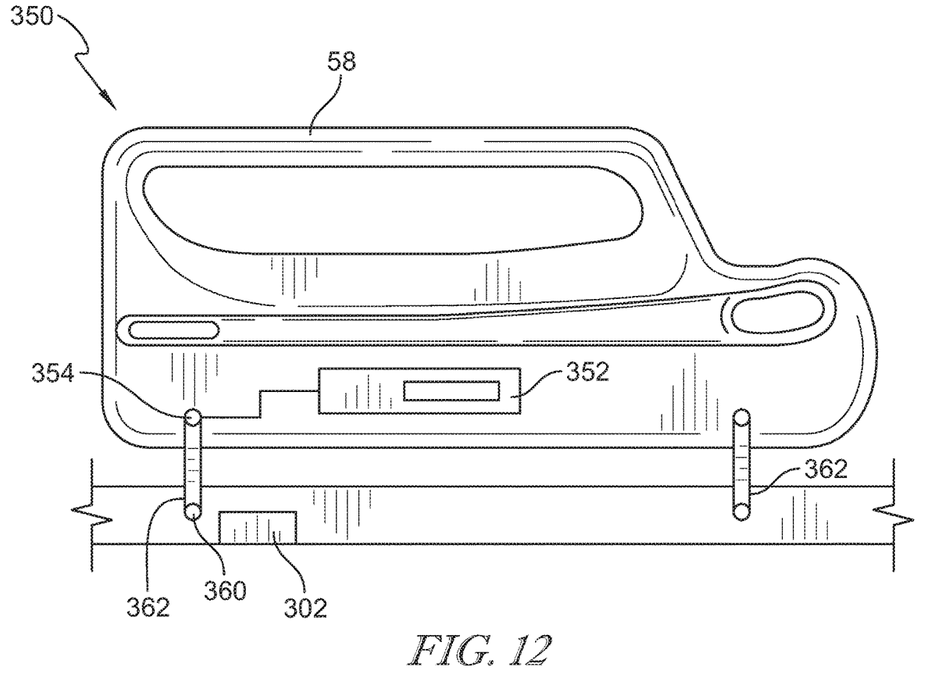
FIG. 12 is a side schematic view of the side rail shown in FIG. 1 coupled to the frame shown in FIG. 1 and an inductive power transmitter positioned on the frame and an inductive power receiver positioned on the side rail.

FIG. 12 illustrates another embodiment of an inductive power system 350 that may be utilized with the power system 300. The power system 350 includes the power supply 302 of the bed 10 and a power transmitter 360. The power transmitter 360 is incorporated into a first end of a hinge 362. In such an embodiment, a side rail 48, 50, 58, and/or 60 includes electronics 352, e.g. the control system 140 and graphical user interface 142. The electronics 352 are coupled to an inductive power receiver 354 in a second end of the hinge 362 so that the electronics 352 are powered by a power signal between the transmitter 360 and the receiver 354. It should be noted that data signals may also be passed between the transmitter 360 and the receiver 354. It will also be appreciated that both the transmitter 360 and the receiver 354 may be transceivers capable of both transmitting and receiving power and data. The hinge 362 provides wireless power and communication and eliminates the need to have another opening/port in the mattress. The hinge 362 also eliminates the need to extend wires between the frame 24 and the respective side rail.

The power systems 300 and 350 provide a data and power solution for measuring the mattress internal climate and for other sensors such as radar that can measure motion, respiration rate, heart rate, and patient immersions. Having these sensors allows better control of the mattress climate to minimize the occurrence of pressure ulcers and also measure respiration data that is typically not correctly measured by nurses. With the automatic vital sign, the reliability of early warning scores is increases and patient outcomes may be improved. Further, respiration depth may be measured for a better understanding of pulmonary health. Patient motion can be measured to provide an automated input for the Braden mobility score. In-mattress radar can image the patient's feet and seat, the motion of which is a strong indicator of impending bed-exit attempts.

It should be noted that the power systems 300 and 350 may also operate with an inductive transmitter positioned in a healthcare facility wall. In other embodiments, the power systems 300 and 350 may be configured to transfer power to or from a remote device, for example a medical cart. It yet another embodiment, the power systems 300 and 350 may be configured to transfer data, for example image data and sensor data.

Although this disclosure refers to specific embodiments, it will be understood by those skilled in the art that various changes in form and detail may be made without departing from the subject matter set forth in the accompanying claims.

The invention claimed is:

1. A patient support apparatus comprising:
   a foam frame defining a space,
   a bladder assembly positioned in the space, the bladder assembly including a plurality of foam filled bladders, each of the foam filled bladders interconnected by a manifold,
   a plurality of mutually exclusively selectable pressure relief valves, wherein a selected pressure release valve of the plurality of selectable pressure release valves is configured to release air from the bladder assembly if a pressure in the bladder assembly exceeds a predetermined limit of the selected pressure relief valve, wherein each selectable pressure release valve releases air at a different predetermined limit,
   a cover that encases the foam frame and the bladder assembly,
   an electronic component positioned within the cover,
   an inductive power receiver positioned within the cover, and
   an inductive power transmitter position outside of the cover,
   wherein the inductive power transmitter transmits a power signal to the power transceiver to supply power to the electronic component.

2. The patient support apparatus of claim 1, further comprising a control knob to select the selected pressure release valve.

3. The patient support apparatus of claim 2, wherein the control knob is manually operated.

4. The patient support apparatus of claim 1, further comprising a weigh scale, wherein the selected pressure relief valve is selected based on a weight of a patient measured by the weigh scale.

5. The patient support apparatus of claim 4, wherein the selected pressure relief valve is automatically selected based on the weight of the patient measured by the weigh scale.

6. The patient support apparatus of claim 1, wherein the plurality of selectable pressure relief valves includes:
a first pressure relief valve having a predetermined limit that corresponds to a first weight of a patient,
a second pressure relief valve having a predetermined limit that corresponds to a second weight of a patient, and
a third pressure relief valve having a predetermined limit that corresponds to a third weight of a patient.

7. The patient support apparatus of claim 6, wherein:
the first weight of a patient is within a range of 70 pounds to 250 pounds,
the second weight of a patient is within a range of 251 pounds to 400 pounds, and
the third weight of a patient is within a range of 401 pounds to 500 pounds.

8. The patient support apparatus of claim 1, wherein:
the bladder assembly includes a first plurality of foam filled bladders and a second plurality of foam filled bladders, and
the plurality of selectable pressure release valves includes a first plurality of selectable pressure relief valves in fluid communication with the first plurality of foam filled bladders and a second plurality of selectable pressure relief valves in fluid communication with the second plurality of foam filled bladders.

9. The patient support apparatus of claim 8, wherein:
a first selected pressure release valve of the first plurality of selectable pressure release valves is configured to release air from the first plurality of foam filled bladders if the pressure in the first plurality of foam filled bladders exceeds a predetermined limit of the first selected pressure relief valve, and
a second selected pressure release valve of the second plurality of selectable pressure release valves is configured to release air from the second plurality of foam filled bladders if the pressure in the second plurality of foam filled bladders exceeds a predetermined limit of the second selected pressure relief valve.

10. The patient support apparatus of claim 9, wherein the predetermined limit of the first selected pressure relief valve is different than the predetermined limit of the second selected pressure relief valve.

11. The patient support apparatus of claim 9, wherein the predetermined limit of the first selected pressure relief valve is the same as the predetermined limit of the second selected pressure relief valve.

12. The patient support apparatus of claim 1, wherein the electronic component includes a digital x-ray cassette.

13. The patient support apparatus of claim 12, wherein the electronic component wirelessly transmits signals to devices positioned outside of the cover.

14. The patient support apparatus of claim 1, further comprising:
a frame, wherein the foam frame and the bladder assembly are positioned on the frame,
a side rail coupled to the frame,
an inductive power transmitter positioned on the frame, and
an inductive power receiver positioned on the side rail,
wherein the inductive power transmitter transmits a power signal to the inductive power receiver to power an electronic component on the side rail.

15. The patient support apparatus of claim 14, wherein the side rail is moveable between a lowered position and a raised position, wherein the inductive power transmitter transmits a power signal to the inductive power receiver when the side rail is in the lowered position or the raised position.

16. A patient support apparatus comprising:
a foam frame defining a space,
a bladder assembly positioned in the space, the bladder assembly including a plurality of foam filled bladders, each of the foam filled bladders interconnected by a manifold,
a plurality of mutually exclusively selectable pressure relief valves, wherein a selected pressure release valve of the plurality of selectable pressure release valves is configured to release air from the bladder assembly if a pressure in the bladder assembly exceeds a predetermined limit of the selected pressure relief valve, wherein each selectable pressure release valve releases air at a different predetermined limit,
a frame, wherein the foam frame and the bladder assembly are positioned on the frame,
a side rail coupled to the frame,
an inductive power transmitter positioned on the frame, and
an inductive power receiver positioned on the side rail,
wherein the inductive power transmitter transmits a power signal to the inductive power receiver to power an electronic component on the side rail.

17. The patient support apparatus of claim 16, wherein the side rail is moveable between a lowered position and a raised position, wherein the inductive power transmitter transmits a power signal to the inductive power receiver when the side rail is in the lowered position or the raised position.

18. The patient support apparatus of claim 16, further comprising a weigh scale, wherein the selected pressure relief valve is selected based on a weight of a patient measured by the weigh scale.

19. The patient support apparatus of claim 16, wherein the plurality of selectable pressure relief valves includes:
a first pressure relief valve having a predetermined limit that corresponds to a first weight of a patient,
a second pressure relief valve having a predetermined limit that corresponds to a second weight of a patient, and
a third pressure relief valve having a predetermined limit that corresponds to a third weight of a patient.

* * * * *